(12) United States Patent
Zhang (10) Patent No.: US 8,233,972 B2
(45) Date of Patent: Jul. 31, 2012

(54) SYSTEM FOR CARDIAC ARRHYTHMIA DETECTION AND CHARACTERIZATION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 183 days.

(21) Appl. No.: 12/899,613

(22) Filed: Oct. 7, 2010

(65) Prior Publication Data

US 2011/0201951 A1 Aug. 18, 2011

Related U.S. Application Data (60) Provisional application No. 61/303,765, filed on Feb. 12, 2010.

(51) Int. Cl.
*A61B 5/04* (2006.01)
(52) U.S. Cl. ...................................................... 600/509
(58) Field of Classification Search .................... 600/509
See application file for complete search history.

(56) References Cited

U.S. PATENT DOCUMENTS

| | | | |
|---|---|---|---|
| 5,439,483 A | 8/1995 | Duong-Van | |
| 5,471,991 A | 12/1995 | Shinnar | |
| 5,778,881 A | 7/1998 | Sun et al. | |
| 6,393,316 B1 | 5/2002 | Gillberg et al. | |
| 6,561,986 B2 | 5/2003 | Baura et al. | |
| 6,572,560 B1 | 6/2003 | Watrous et al. | |
| 6,925,324 B2 * | 8/2005 | Shusterman | 600/509 |
| 6,993,377 B2 | 1/2006 | Flick et al. | |
| 7,062,314 B2 * | 6/2006 | Zhu et al. | 600/515 |
| 7,171,269 B1 | 1/2007 | Addison et al. | |
| 7,369,889 B2 | 5/2008 | Astrom et al. | |
| 2004/0193067 A1 | 9/2004 | Hayek et al. | |
| 2007/0191725 A1 | 8/2007 | Nelson | |
| 2007/0260152 A1 | 11/2007 | Ghanem et al. | |
| 2008/0015452 A1 | 1/2008 | Ricci et al. | |
| 2008/0109041 A1 | 5/2008 | DeVoir | |

OTHER PUBLICATIONS

Ag Ramakrishnan and Supratin Saha, "ECG Coding by Wavelet-Based Linear Prediction" IEEE Transactions on Biomedical Engineering, 1997, 44 (12), pp. 1253-1261.
S. Almagro et al., "A new mother wavelet for fetal ECG to achieve optimal denoising and compressing results", Proc. 33rd Annual International Conference on Computers in Cardiology, Valencia, Spain, Sep. 17-20, 2006, pp. 157-160.
C Saritha, et al., "ECG Signal Analysis Using Wavelet Transforms", Bulg. J. Phys. 2008, 35: pp. 68-77.
L. Senhadji et al., "Comparing Wavelet transforms for Recognizing Cardiac Patterns", IEEE Engineering in Medicine and Biology Magazine, Publication date: Mar./Apr. 1995, vol. 14, Issue: 2, on pp. 167-173.

* cited by examiner

*Primary Examiner* — George Manuel
(74) *Attorney, Agent, or Firm* — Alexander J Burke

(57) ABSTRACT

A system for heart performance characterization and abnormality detection includes an interface that receives a signal representing electrical activity of a patient heart occurring during individual heart cycles of multiple sequential heart cycles. A signal processor decomposes the received signal into multiple signals comprising a heart cycle signal primary wave and one or more heart cycle signal wavelets occurring at corresponding successively higher frequencies. The signal processor determines multiple amplitude representative values of the heart cycle signal primary wave and the one or more heart cycle signal wavelets. A comparator compares the multiple amplitude representative values with corresponding multiple predetermined threshold values to provide comparison indicators. A patient monitor in response to the comparison indicators indicating at least one of the amplitude representative values exceeds a respective predetermined threshold value, generates an alert message associated with the respective predetermined threshold.

19 Claims, 6 Drawing Sheets

SYSTEM FOR CARDIAC ARRHYTHMIA DETECTION AND CHARACTERIZATION

This is a non-provisional application of provisional application Ser. No. 61/303,765 filed Feb. 12, 2010, by H. Zhang.

FIELD OF THE INVENTION

This invention concerns a system for heart performance characterization and abnormality detection by decomposing a patient heart signal into multiple wavelet signals and determining characteristics of the wavelet signals.

BACKGROUND OF THE INVENTION

Cardiac arrhythmia analysis and characterization are used for the management of cardiac disorders and irregularities. Cardiac electrophysiological (EP) activities can be used to sense, monitor and diagnose cardiac arrhythmia and pathology related abnormality. For example, P wave disorders for atrial fibrillation (AF) and ST segment changes for myocardial ischemia and infarction. However, cardiac pathology related electrophysiological signal and waveform changes are small and difficult to extract, especially in the early stages of a cardiac abnormality or event. Additionally, known clinical methods for ECG or intra-cardiac electrogram analysis may not efficiently diagnose a signal waveform singularity or diagnose irregular changes caused by cardiac arrhythmia, especially sub-waveform changes in electrophysiological signals.

Early arrhythmia recognition and characterization, such as of myocardial ischemia and infarction, is desirable for rhythm management and treatment of cardiac disorders and irregularities. Known systems use waveform morphologies and time domain parameter analysis of depolarization and repolarization, including P wave, QRS complex, ST segment, T wave, for cardiac arrhythmia monitoring and identification. However, known systems are often subjective and time-consuming, and require expertise and clinical experience for accurate interpretation and proper cardiac rhythm management. Known systems fail to provide sufficient information on cardiac electrophysiological function and activity interpretation, tissue mapping and arrhythmia localization.

Additionally, known systems typically focus on time (amplitude, latency) or frequency (power, spectrum) domain changes and analysis. This may fail to capture and characterize small signal changes in a partial portion (P wave, QRS complex, ST segment) of a cardiac activity signal and are usually invisible in a signal waveform or need extensive clinical expertise to correctly diagnose. In cardiac arrhythmia cases (especially in an early stage, such as myocardial ischemia, ventricular tachycardia), signal changes are hidden inside electrograms. In early stages of cardiac arrhythmia, pathology and event related signal changes are small and not easy to detect. Known systems typically fail to qualitatively and quantitatively capture and characterize such small changes, and predict a pathological trend. Known systems typically fail to identify in real time a growing trend of a cardiac arrhythmia, such as a pathology trend from low risk to medium, and then to high risk (severe and fatal) rhythm (especially for an arrhythmia, such as VT (ventricular tachycardia) and myocardial infarction (MI)). Known systems for cardiac arrhythmia calculation and evaluation generate inaccurate and unreliable data and results because of unwanted noise and artifacts. Environmental noise and patient movement artifacts, such as electrical interference, can distort a waveform and make it difficult to detect R wave and ST segment elevation accurately, and generate false alarms. A system according to invention principles addresses these deficiencies and related problems.

SUMMARY OF THE INVENTION

A system decomposes ECG signals (including wavelet complex spectrum, wavelet complex vector decomposition) to detect and characterize electrophysiological abnormalities and map electrophysiological signal wavelet variation and distribution to cardiac conditions and clinical events. A system for heart performance characterization and abnormality detection includes an interface that receives a signal representing electrical activity of a patient heart occurring during individual heart cycles of multiple sequential heart cycles. A signal processor decomposes the received signal into multiple signals comprising a heart cycle signal primary wave and one or more heart cycle signal wavelets occurring at corresponding successively higher frequencies. The signal processor determines multiple amplitude representative values of the heart cycle signal primary wave and the one or more heart cycle signal wavelets. A comparator compares the multiple amplitude representative values with corresponding multiple predetermined threshold values to provide comparison indicators. A patient monitor in response to the comparison indicators indicating at least one of the amplitude representative values exceeds a respective predetermined threshold value, generates an alert message associated with the respective predetermined threshold.

DETAILED DESCRIPTION OF THE INVENTION

A system improves precision and reliability of analysis and interpretation of cardiac electrophysiological activities by analyzing and characterizing cardiac function signals (including surface ECG signals and intra-cardiac electrograms) based on ECG signal complex analysis, mode and pattern diagnosis, characterization and mapping. The system uses ECG complex based signal decomposition (including complex wavelet spectrum, wavelet complex vector) to detect and characterize electrophysiological abnormality and singularity. The system extracts and maps electrophysiological signal wavelet complex variation and distribution of cardiac activities to corresponding medical conditions. The system identifies cardiac disorders, differentiates cardiac arrhythmias, characterizes pathological severity, predicts life-threatening events, and evaluates drug delivery and effects.

In cardiac arrhythmia cases (especially in early stage cases, such as myocardial ischemia, ventricular tachycardia), changes are hidden inside electrogram signals. Signal decomposition is used to reveal such changes. Wavelet and time-frequency analysis are useful to extract pathology related small signal changes in electrogram waveforms. However, wavelet analysis may fail to efficiently perform ECG waveform diagnosis and singularity information extraction. A system according to invention principles provides a series of ECG wavelet complex signals for cardiac signal analysis and clinical evaluation of a heart and circulation system.

Cardiac electrophysiological wavelet complex based calculation and analysis is used to capture and characterize cardiac function related information and to acquire detailed information on severity of pathology, location of an abnormal function and tissue (such as muscle, chamber). Wavelet decomposition methods may use Harr wavelet or Gabor wavelet methods, for example, which may not be efficient for cardiac electrophysiological signal analysis. The ECG signal wavelet complex analysis facilitates categorizing electrophysiological signals comprising fast and slow waveforms and to capture acute and early changes and abnormality within cardiac signals for detection of acute AF and acute ischemia events. System signal wavelet complex analysis decreases noise and artifact effects, such as noise from power line and patient respiration and is used for evaluation of medical treatment and drug delivery. The system cardiac signal wavelet complex decomposition and analysis may be implemented in implantable cardiac devices and be used for multi-channel cardiac electrophysiological signal diagnosis (function mapping), such as of intra-cardiac signals derived from different leads of a multi-lead catheter and multiple catheters. Additionally the system cardiac signal wavelet complex calculation and diagnosis may also be utilized for other kinds signal processing which may involve biological force or oximetric signal analysis, such as of hemodynamic blood pressure signals, SPO2 blood flow signals and vital sign signals.

In response to occurrence of abnormality or a clinical event, cardiac tissue is often affected and a pacing excitation energy conduction mechanism is impacted and exhibits abnormal variation. The system electrophysiological signal complex mode and pattern analysis interprets depolarization and repolarization signal variation (data and waveform variation in both time and frequency domain), to detect cardiac arrhythmias, characterize pathological severity, predict life-threatening events, and evaluate drug delivery and effects. The system employs electrophysiological signal wavelet complex based decomposition, wavelet vector based cardiac function analysis and multi-channel (anatomical site) electrophysiological signal wavelet pattern analysis to identify heart and circulation conditions. The system maps derived wavelet data to medical conditions in 2D and 3D cardiac image data and representations.

Wavelet analysis and calculation may employ Harr wavelet or Gabor wavelet functions to perform mathematical decomposition to decompose an electrophysiological signal into different levels (time-frequency combined domain analysis) and sub-waveforms (wavelets). However such wavelet analysis does not consider ECG signal characteristics and sometimes fails to detect small changes within ECG signals because analysis provides a mother waveform that does not perfectly match an ECG signal and distributes the signal into different level wavelets. This may generate noise and artifacts and cause unexpected singularities and false abnormality detection. The system provides ECG signal mother wave based decomposition improving matching and level decomposition. In response to a cardiac pathology event or early arrhythmia, cardiac tissue and cells may operate with a different rhythm compared with other cells, such as cells from atrial fibrillation tissue or myocardial ischemia tissue. Excitation transition time and energy may vary (be faster or slower), which may cause different level wavelets in the signals and show some noise and artifacts in the electrophysiological activities, such as ST elevation in Myocardial Infarction (MI) cases. The system performs ECG signal complex based multi-level decomposition and processes different level ECG waveforms to characterize small changes and to predict cardiac events and arrhythmias.

Figure 1:
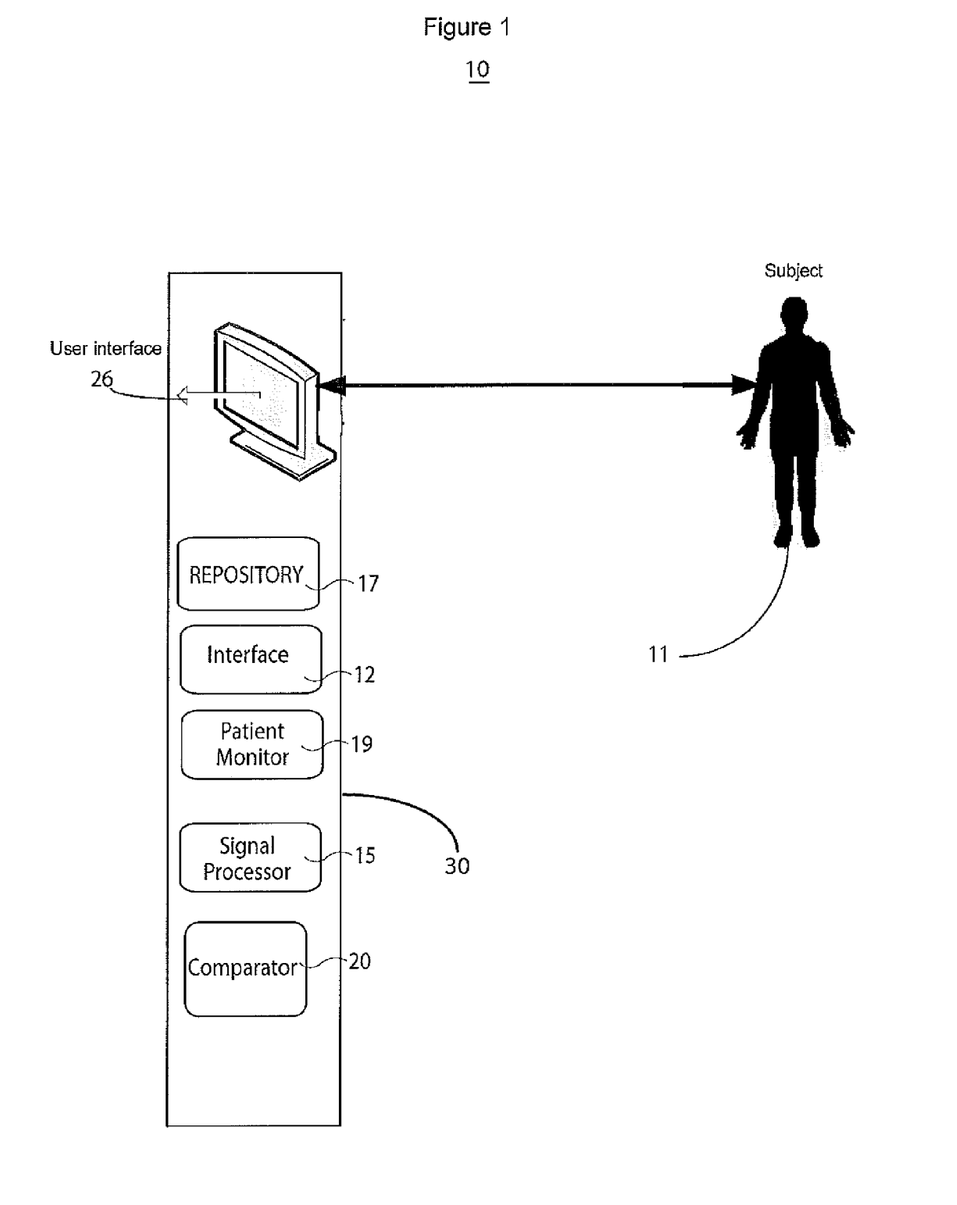
FIG. 1 shows a system for heart performance characterization and abnormality detection, according to invention principles.

FIG. 1 shows system 10 for heart performance characterization and abnormality detection. System 10 analyzes electrophysiological signals (including surface ECG, intra-cardiac electrograms, and heart activity signals, such as a cardiac sound waveform) by decomposing the signal into multiple wavelet signals and determining characteristics of the wavelet signals. System 10 comprises at least one computer system, workstation, server or other processing device 30 including interface 12, repository 17, patient monitor 19, signal processor 15, comparator 20 and a user interface 26. Interface 12 receives a signal representing electrical activity of a patient 11 heart occurring during individual heart cycles of multiple sequential heart cycles. Signal processor 15 decomposes the received signal into multiple signals comprising a heart cycle signal primary wave (mother wave) and one or more heart cycle signal wavelets occurring at corresponding successively higher frequencies. Signal processor 15 determines multiple amplitude representative values of the heart cycle signal primary wave and the one or more heart cycle signal wavelets. Comparator 20 compares the multiple amplitude representative values with corresponding multiple predetermined threshold values to provide comparison indicators. Patient monitor 19, in response to the comparison indicators indicating at least one of the amplitude representative values exceeds a respective predetermined threshold value, generates an alert message associated with the respective predetermined threshold.

Figure 2:
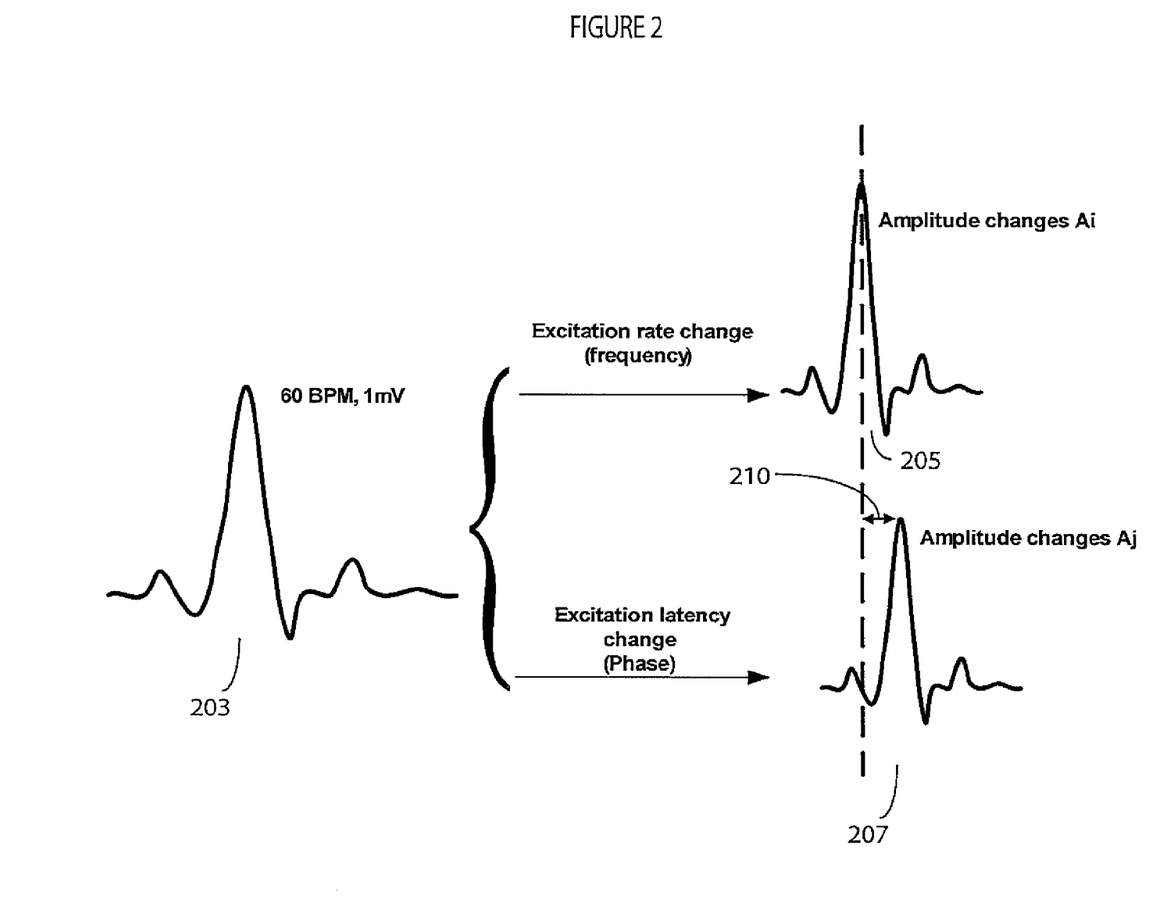
FIG. 2 shows an ECG signal mother wave decomposition into different level ECG signal based wavelet (sub-waves), according to invention principles.

FIG. 2 shows ECG signal decomposition into different level ECG signal based wavelet (sub-waves). System 10 decomposes an ECG signal into a standard normal ECG signal mother wave 203 (60 BPM (beats per minute), 1 mV amplitude) and sub waves 205 and 207 (different level wavelets). The cardiac mechanism involves heart tissue cells working in excitation rhythm and the cells usually have a similar rhythm waveform shape and morphology. The electrophysiological activity of some cells is faster (building waves called fast waves) and electrophysiological activity of some of the cardiac cells is slower (building waves called slow waves). Cardiac signals (ECG, ICEG, and electrophysiological responses) may be considered to be a combination of these faster and slower waves and wavelets. System 10 categorizes decomposed mother wave 203 and different level wavelets 205 and 207, for example, to thereby characterize the associated electrophysiological signal and to identify signal changes. Mother waveform 203 is from ECG Lead II but different leads (such as ECG lead V1, V2, for example) may provide a different ECG mother wave. A patient normal electrophysiological signal (rather than one exhibiting abnormality) is used as a baseline mother wave, to improve detection of abnormality and difference from a mother wave exhibiting abnormality. In comparison with Gabor or Harr wavelet decomposition and analysis, ECG signal decomposition extracts data indicating pathological anatomically related changes having a physical meaning, e.g., particular tissue giving a fast wave or cardiac malfunction points.

System 10 in one embodiment, decomposes different kinds of ECG signals into different level ECG wavelets per the function, $$\text{ECG\_signal} = \sum_{i \in N} A_i w_i(\text{rate}, \text{mag}, \text{phase}) \quad \text{equation 1}$$

Where $w_i(\text{rate,mag,phase})$ is the different level ECG complex wavelet base (in which rate is the beat; mag is the magnitude (peak to peak amplitude) of the wavelet signal; and phase is latency e.g. phase delay 210); $A_i$ is the coefficient of decomposition in each level; N is number of the decomposition level which can be controlled adaptively in the system. An ECG signal in equation 1 can be a signal comprising one single heart beat, for example from P wave to P wave, or a multi-beat signal, or an averaged heart beat signal. In order to achieve simplified and complete decomposition, the ECG signal complex wavelet is quantized from the mother wavelet 203. For example if mother waveform 203 is 60 beats per minute, a wavelet may be 120 or 180 beats per minute, for example. Equation 1 indicates wavelets of the same level may have different base waveforms having different phase characteristics. In the case that there is only one wavelet base in each level, a coefficient series may be constructed into a vector; in the case there is more than one wavelet base in each decomposition level, a coefficient series may be constructed into one matrix (each column standing for one level, different rows in the same column standing for the basis and having different phase).

In order to get the best decomposition and optimize the decomposition level, the difference between the original signal and decomposition is controlled mathematically by the condition, $$\Delta = \sum_{j \in \text{signal\_range}} \|\text{ECG\_signal}^j - A_i w_i(\text{rate}, \text{mag}, \text{phase})^j\|^2 \leq \delta \quad \text{equation 2}$$

In which, j is the data sample in the waveform; δ is the maximum difference between the original signal and decomposed signal. Based on clinical application sensitivity and accuracy requirement, usually δ is $10^{-5}$ or less. System 10 decomposes each ECG signal into a series of amplitude coefficient difference representative values representing differences between a normal and abnormal ECG signal using the above ECG complex decomposition method and equation 2. The coefficients are constructed into a matrix or a vector, which is used for real time comparison and tracking of level changes.

Figure 3:
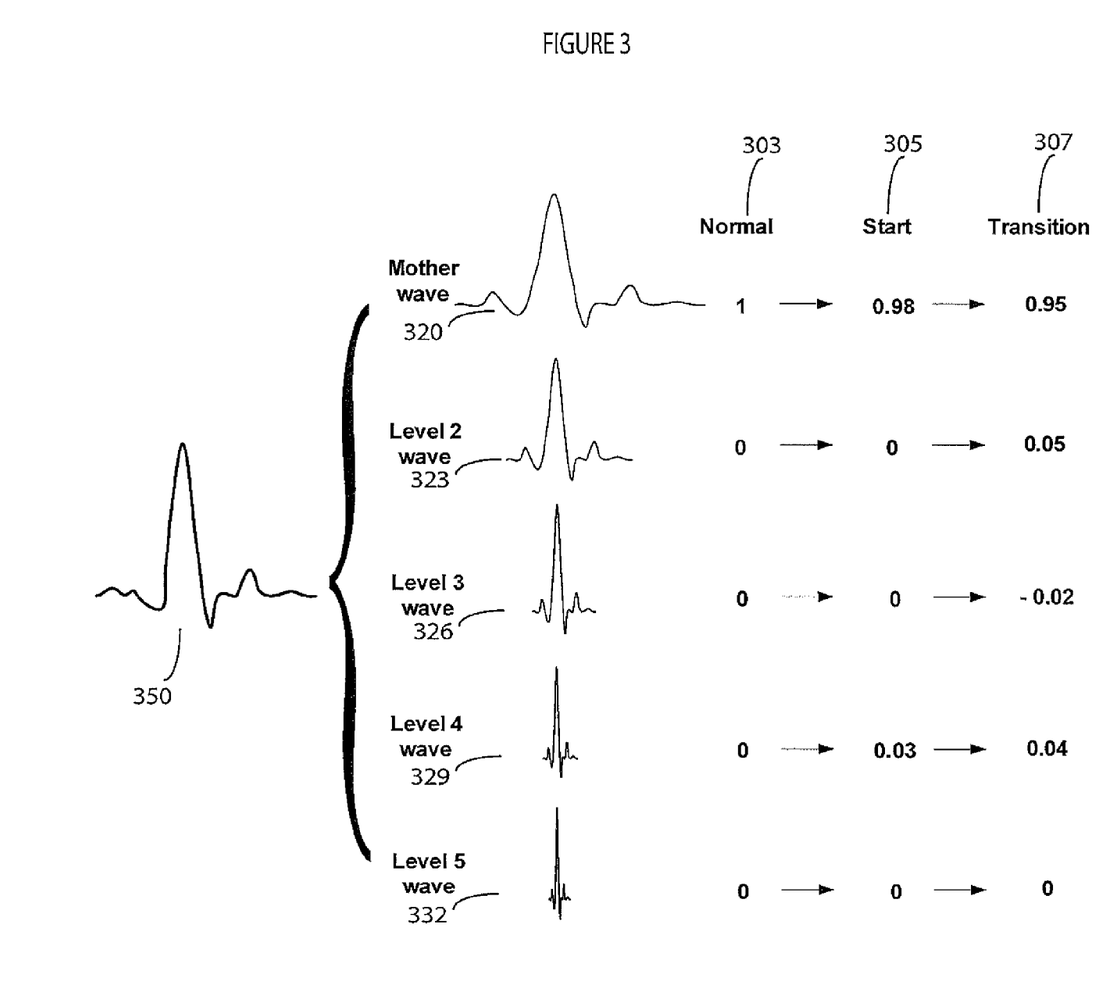
FIG. 3 shows decomposition of an early stage atrial fibrillation signal into ECG signal complex wavelets, according to invention principles.

FIG. 3 shows decomposition by system 10 (FIG. 1) of an early stage atrial fibrillation signal into ECG signal complex wavelets. In an emerging AF case, for example, a normal healthy heart beat is 60 BPM (in this example), amplitude 1 mV and is decomposed in response to user selection of N=5 with $\delta=10^{-5}$ in equation 2. ECG signal 350 is decomposed into mother wave 320 and wavelets 323, 326, 329, 332 of successively increasing level (levels 2, 3, 4 and 5). Mother wave 320 is derived from a normal healthy (benign) heart beat ECG of the same patient. The different levels of the ECG signal complex wavelets are 120 BPM and 180 BPM. Columns 303, 305 and 307 indicate amplitude representative values of a heart cycle signal primary (mother) wave and wavelets 323, 326, 329, 332. Specifically, amplitude representative values in column 303 for the different wavelet levels are values for a normal heart. Amplitude representative values in column 305 for the different wavelet levels are values indicating start of atrial fibrillation and amplitude representative values in column 307 for the different wavelet levels indicate transition and increasing severity of the cardiac condition. System 10 detects change (and variability) in amplitude representative values for the different level wavelets to detect and track patient health status during a cardiac procedure and for cardiac monitoring.

A baseline (pre-determined normal signal or benign signal) beats per minute (BPM) value of the mother ECG wave is determined and used to generate different level wavelets (the wavelets BPM values are determined based on the mother wave comprising double, triple the mother wave BPM, for example). System 10 analyzes different levels by performing an energy value comparison for the different wavelet levels, a spectrum distribution value comparison for the different wavelet levels, a signal variation and variability value comparison for the different wavelet levels, for example. Most energy (e.g. 99%) in a decomposed normal healthy cardiac signal is found in the first few levels (e.g., levels 1 or 2). The more levels and more complex wavelet components appearing in a decomposition, the more complex is the original signal. This also reflects the bifurcation characteristics in heart operation and indicates future cardiac arrhythmias and events. System 10 adaptively employs different signal processing methods for pattern analysis, signal energy calculation, complexity calculation and cardiac rotor analysis.

As illustrated in FIG. 3, for a healthy heart beat, an amplitude coefficient matrix is [1, 0, 0, 0, 0]. When there is an emerging AF signal, the decomposition amplitude coefficient matrix becomes [0.98, 0, 0, 0.03, 0] and after some time AF is more obvious, the decomposition amplitude coefficient matrix is [0.95, 0.05, −0.02, 0.04, 0], for example. The amplitude coefficients are distributed in different wavelet levels and matrices indicating more irregular ECG wavelets are emerging and fibrillation in the atrium is becoming more serious. In a complicated case, such as ventricular tachycardia and fibrillation signal analysis, there may be a multi wavelet complex component in the same level (which means the wavelet has the same frequency or heart rate as the mother wave BPM) but with different phase (latency). In these cases, the system compares variation in components in the same level. For example, in an energy comparison, the following equation is used to compute energy in wavelet level i:

$$\text{signal\_complex\_wavelet}_i = \sum_{j \in M} A_{ij} w_{ij}$$

Where, M is the number of complex wavelets in the level i; $A_{ij}$ is the coefficient for different wavelet in level i; $w_{ij}$ is the different wavelet in the same level i but with different phase, (the number of complex wavelets reflects the complexity and randomness of signal changes and variation).

In a complicated case, if there are different wavelet complex components in each level, a matrix is built for pattern analysis of electrophysiological signals in different levels (including frequency or phase based matrix and vector analysis). The analysis includes variation, spectrum, energy and pattern analysis. The decomposition can also be used for signal reconstruction to cancel artifacts and improve noise immunity and singularity detection. As an example wavelet component $A_{23}w_{23}$ can be removed in a signal reconstruction to improve signal to noise ratio.

A decomposition may be used to track fast or slow shifts in a waveform, for example, from 180 BPM to 120 BPM and detects disappearance of a wavelet (e.g., of 120 BPM), for example. This indicates electrophysiological changes and variation within tissue and is used to evaluate cardiac events, such as ablation effects and drug delivery. System 10 (FIG. 1) performs continuous calculation and monitoring of decomposed wavelets of a signal including of individual decomposition level coefficients. System 10 calculates different kinds of frequency (beat rate) and excitation energy changes and performs pattern analysis, statistical calculation including of deviation, complexity analysis (such as nonlinear dynamic and approximate entropy) and entropy calculation (Shannon entropy, wavelet entropy), for example. The values of columns 303, 305 and 307 of FIG. 3 (e.g. peak detected) amplitude values are determined at successive time intervals of mother wave 320 and wavelets 323, 326, 329 and 342 which may or may not occur at harmonics or half-harmonics (or other frequencies) for example.

Figure 4:
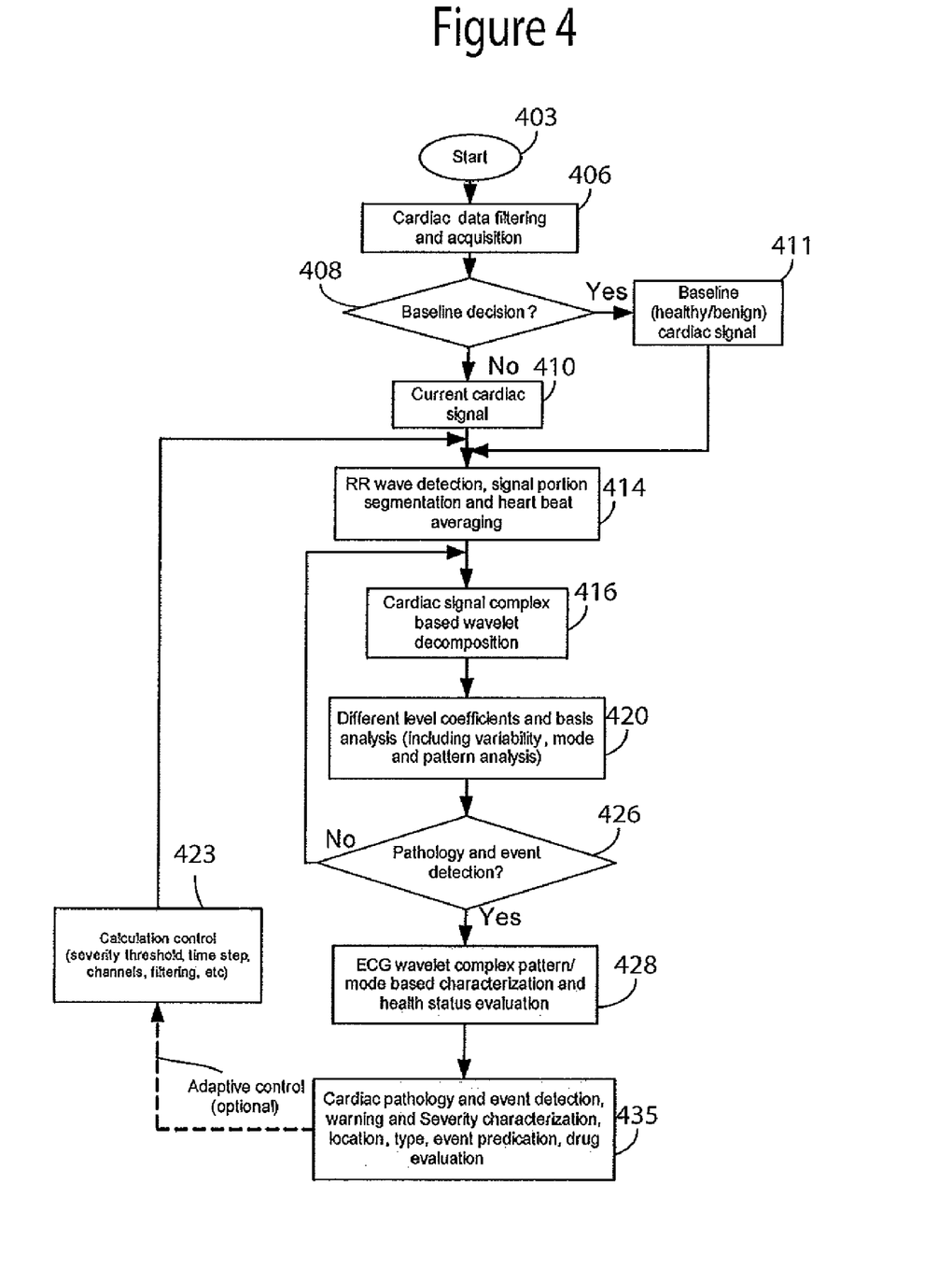
FIG. 4 shows a flowchart of a process for electrophysiological signal complex wavelet based calculation, detection and interpretation, according to invention principles.

FIG. 4 shows a flowchart of a process for electrophysiological signal complex wavelet based calculation, detection and interpretation performed by system 10. This provides relatively early determination of location, timing, severity, type of cardiac pathology and disease by analyzing different wavelet complex signals acquired from different leads of a multi-lead catheter. Following the start at step 403, interface 12 in step 406 acquires digitized electrophysiological signals from multiple channels of a multi-channel intra-cardiac (e.g., basket) catheter indicating electrical activity at multiple cardiac tissue sites. Interface 12 filters the acquired electrophysiological signals using a filter adaptively selected in response to data indicating clinical application (e.g. ischemia detection, rhythm analysis application) and in step 408 determines whether a baseline level has already been determined for a current filtered signal 410. If a baseline level has not been selected, a baseline cardiac signal level for a benign healthy heart is selected in step 411 by interface 12 for use in beat to beat wavelet complex comparison. In step 414, signal processor 15 performs signal pre-analysis by identifying different segments (QRS, ST, P wave, Q wave, R wave, S wave, ST segment, T wave, U wave segments, for example) of the current cardiac signal 410 or selected baseline cardiac signal and averages and filters segmented signals.

In step 416, signal processor 15 decomposes the filtered segmented electrophysiological signal into multiple signals comprising a heart cycle signal primary wave and one or more heart cycle signal wavelets occurring at corresponding successively higher frequencies. In step 420 signal processor 15 determines multiple amplitude representative values of the heart cycle signal primary wave and the one or more heart cycle signal wavelets. Processor 15 performs real time cardiac signal complex wavelet analysis by calculating coefficient variation, wavelet complex basis, and amplitude coefficient variability (e.g., from corresponding healthy abnormality-free, baseline amplitude coefficients). In step 426, comparator 20 compares the amplitude representative values with corresponding multiple predetermined threshold values to provide comparison indicators. Signal processor 15 in step 428 employs mapping information in repository 17, associating ranges of the amplitude representative values with corresponding medical conditions in determining patient medical conditions, events and patient health status by comparing the amplitude representative values with the ranges to provide a comparison indicator identifying a medical condition. The comparison indicator triggers a warning and further CRM (cardiac rhythm management) intervention.

If signal processor 15 and comparator 20 in step 428 determine a medical condition indicating cardiac impairment or another abnormality is identified, patient monitor 19 in step 435 generates an alert message identifying the medical condition and abnormality and communicates the message to a user. Processor 15 also determines the severity and location of the condition. Processor 15 in step 423 adaptively adjusts calculation time step, the selected portions and ROI of a filtered signal analyzed and adjusts a threshold employed by comparator 20 to improve medical condition detection and for performance of the process from step 414. If signal processor 15 and comparator 20 in step 426 does not identify a medical condition, the process is repeated from step 416.

In another embodiment a different decomposition function is used such as a function based on sub level or sub wave analysis for signal abnormality and event detection and characterization, such as a Fourier decomposition, wavelet decomposition or empirical decomposition function. The detection of signal abnormality is not limited to coefficient matrix or vector changes (a matrix or vector includes different decomposition level amplitude coefficients). The detection may be used for different individual level sub harmonics or sub wavelet levels. System 10 decomposes an ECG signal waveform, for example, into different level wavelets or harmonics and these harmonics are used individually and in combination to detect and characterize changes in the signal abnormality since small changes due to cardiac pathology reflect individual harmonic and sub wavelet level changes, especially in an early stage of cardiac arrhythmia. System 10 uses different level harmonics and sub wavelets to track and quantify small ECG changes and deviation, for example, by comparing changes with a predetermined threshold (e.g., having a plus or minus 10% threshold).

System 10 selects a baseline signal (waveform) of a healthy heart and compares wavelet amplitude coefficients of a current cardiac signal with the baseline signal wavelet amplitude coefficients. System 10 in one embodiment employs different threshold values for warning and event detection at different anatomical sites, such as external surface ECG signal, ICEG signals, for example. Similarly, system 10 adjusts thresholds in response to data indicating environment (such as noise) and clinical application or treatment involved. System 10 also uses different kinds of signals, electrophysiological signals, vital signs signals (such as ECG, ICEG, SPO2) for signal wavelet analysis. System 10 determines significant signal portions and time stamps in identifying atrial activity, ventricle activity. Furthermore, sub-waveform data and morphology calculations are used to evaluate and characterize patient health and cardiac function status. Also, in response to clinical application, system 10 employs statistical calculation and related hypothesis (such as a T test) for quantification of stages of cardiac pathologies.

System 10 performs multi-channel electrophysiological signal wavelet pattern (vector) analysis and identifies the condition of individual anatomical sites in a 2D or 3D image representation of a heart. The ECG signal based wavelet complex decomposition and calculation is used for catheter multi-channel analysis, such as of ECG lead I, II, III, V1, V2, for example. This may also be used for electrophysiological data and activities, such as ICEG (intra-cardiac electrogram) signals, for example. Additionally multi-channel cardiac wavelet signals are used in combination to improve cardiac condition diagnosis and abnormality location determination.

System 10 uses catheter multi-channel cardiac signal wavelet analysis for internal (local heart system) and global (patient blood circulation system) condition diagnosis by mapping wavelet characteristics to medical conditions. System 10 monitors cardiac electrophysiological operation in real time. In one application, system 10 monitors multi-site cardiac wavelet signals for CCU (critical care unit) and ICU (intensive care unit) patients, who may have a high risk of thrombosis or hemorrhage to control risk and monitor effect of drug delivery i.

Figure 5:
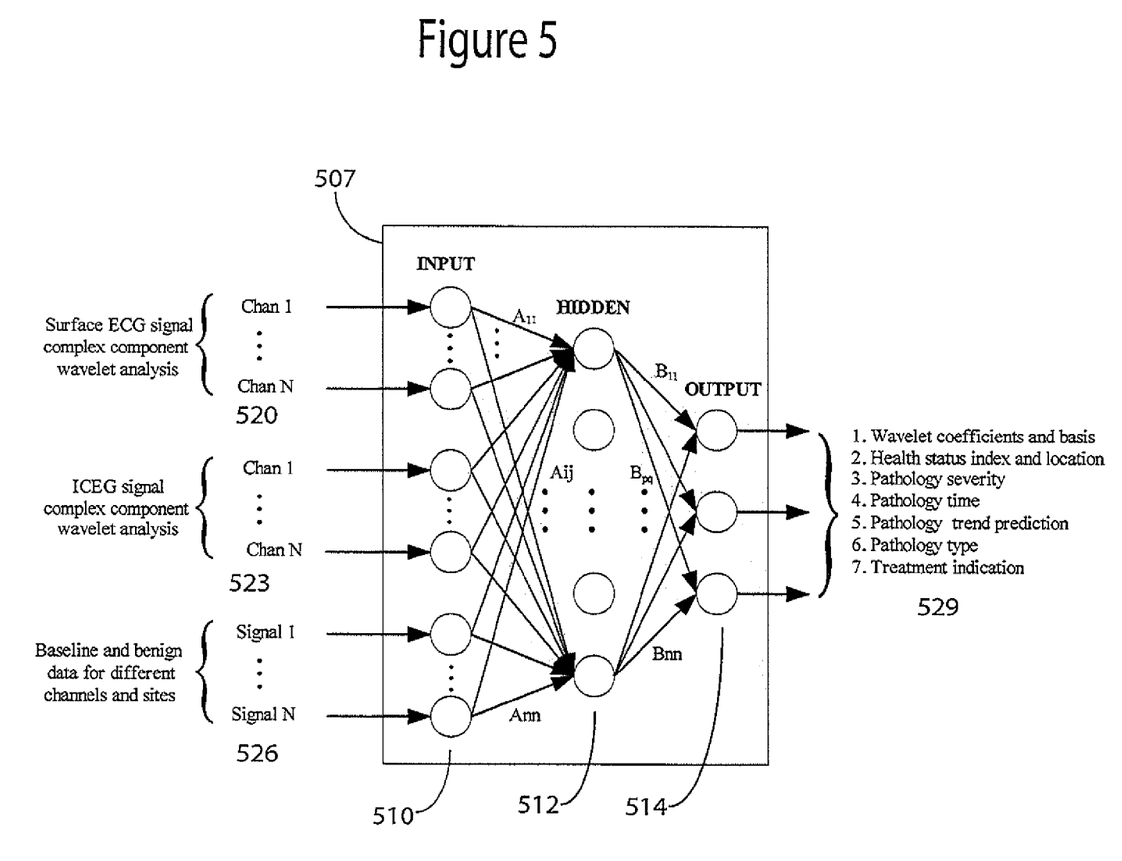
FIG. 5 shows an artificial neural network (ANN) used for multi-channel cardiac signal complex wavelet analysis, according to invention principles.

FIG. 5 shows an artificial neural network (ANN) used for multi-channel cardiac signal complex wavelet analysis, internal and external cardiac signal combination and integration. ANN unit 507 performs multi-channel cardiac signal wavelet analysis to provide information including, arrhythmia event timing, event severity, event localization, candidate treatment suggestion and identifies cardiac disorders. ANN unit 507 processes baseline wavelet data 526 in deriving wavelet amplitude coefficients for multiple anatomical site (multi-catheter channels) ECG and ICEG signals. ANN unit 507 maps one or more surface ECG decomposed wavelet amplitude coefficient values 520 and maps one or more intra-cardiac electrogram (ICEG) decomposed wavelet amplitude coefficient values 523 to, output parameters 529. Output parameters 529 include wavelet amplitude coefficients and corresponding healthy condition (basis) values, corresponding anatomical site location data, a patient health status index, a pathology severity indicator, a time of a cardiac event, a pathology trend indication, a pathology type indication and candidate treatment suggestions. ANN unit 507 structure comprises 3 layers, an input layer 510, hidden layer 512 and output layer 514. ANN unit $A_{ij}$ weights are applied between input layer 510 and hidden layer 512 components of the ANN computation and $B_{pq}$ weights are applied between hidden layer 512 and calculation index components 514 of the ANN computation. The $A_{ij}$ weights and $B_{pq}$ weights are adaptively adjusted and tuned using a training data set. ANN unit 507 incorporates a self-learning function that processes signals 520, 523 and 526 to increase the accuracy of calculated results.

ANN unit 507 processes and maps input signals 520, 523 and 526 to a candidate diagnosis or treatment suggestion 529 to localize a tissue impairment within an organ and determine time of occurrence within a heart cycle. ANN unit 507 also identifies arrhythmia type (e.g., AF, MI, VT, VF), severity of arrhythmia treatment and urgency level and is usable for automatic heart condition detection, diagnosis, warning and treatment. Further unit 507 performs statistical analysis to construct a threshold used to detect tissue impairment and diagnose and predict cardiac arrhythmia and pathology.

Following a training phase with a training data set, ANN unit 507 maps signals 520, 523 and 526 to data 529 indicating an Arrhythmia type, Arrhythmia severity, candidate treatment suggestions, localized tissue impairment information identifying the cardiac arrhythmia position, pathology conducting sequence, abnormal tissue area and focus of the disorder and irregularity, for example. The severity threshold of a pathology mapping decision may vary from person to person and is adjusted at the beginning of analysis. The system may be advantageously utilized in general patient monitoring and implantable cardiac devices for real time automatic analysis and detection of cardiac arrhythmias and abnormalities. ANN unit 507 is particularly useful in multi-channel wavelet analysis and pattern analysis, for cross channel comparison and to further define arrhythmia type and location.

Figure 6:
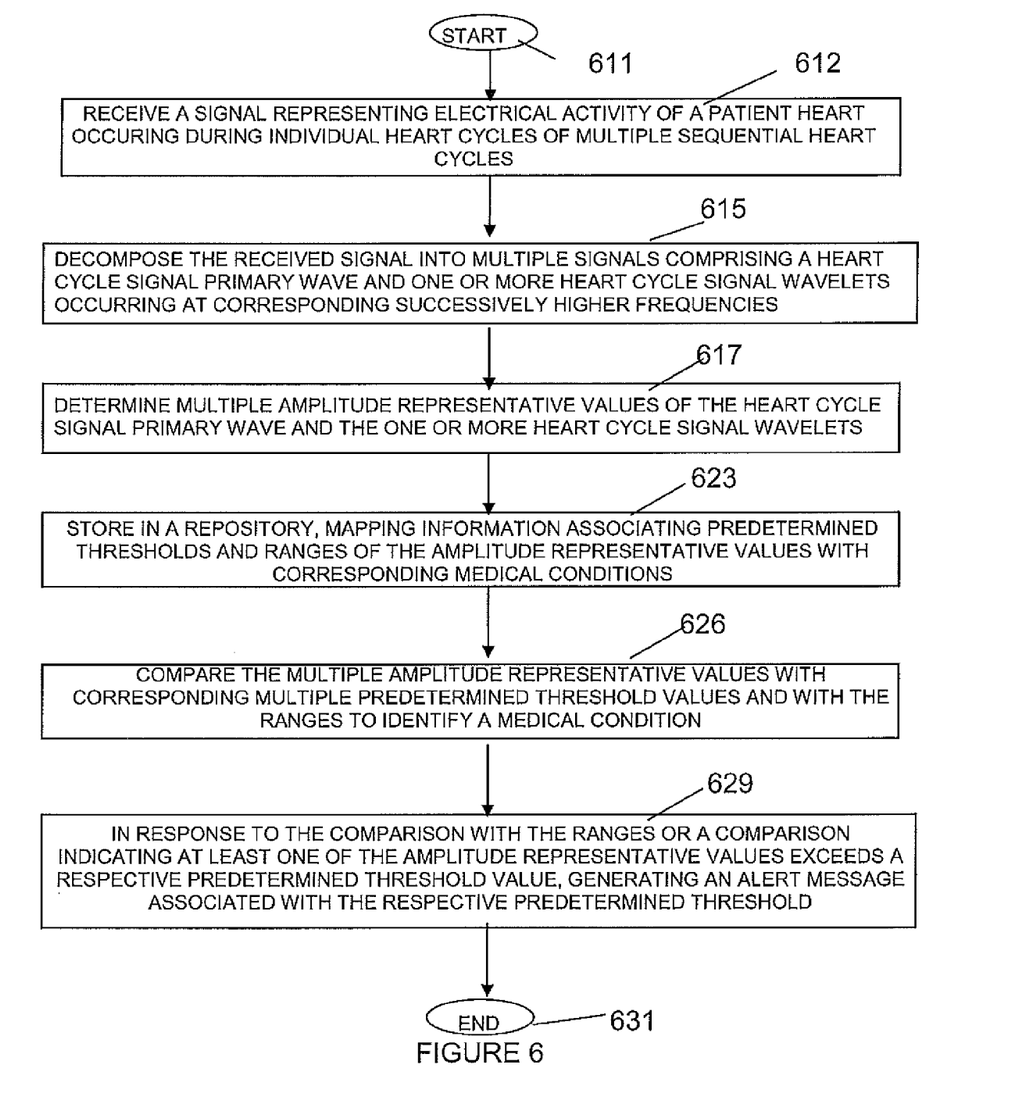
FIG. 6 shows a flowchart of a process used by a system for heart performance characterization and abnormality detection, according to invention principles.

FIG. 6 shows a flowchart of a process used by system 10 (FIG. 1) for heart performance characterization and abnormality detection. In step 612 following the start at step 611, interface 12 receives a signal representing electrical activity of a patient heart occurring during individual heart cycles of multiple sequential heart cycles. The signal representing electrical activity of a patient heart comprises digitized sampled data values and the multiple sequential heart cycles are successive heart cycles. Signal processor 15 filters the received signal and segments the filtered received signal into heart cycle segments including an ST segment. Signal processor 15 in step 615 measures the multiple amplitude representative values by decomposing the received signal into multiple signals comprising a heart cycle signal primary wave and one or more heart cycle signal wavelets occurring at corresponding successively higher frequencies substantially comprising harmonic frequencies of the primary wave. The successively higher frequencies comprise at least one of, (a) harmonics of the primary wave, (b) half-harmonics of the primary wave and (c) intermediate frequencies between harmonics of the primary wave.

In step 617 signal processor 15 determines multiple amplitude representative values of the heart cycle signal primary wave and the one or more heart cycle signal wavelets. The amplitude representative values of the heart cycle signal primary wave and the one or more heart cycle signal wavelets comprise at least one of, (a) a peak amplitude, (b) a mean amplitude value, (c) a median amplitude value and (d) a root mean square amplitude value. Processor 15 also dynamically adjusts at least one of the predetermined threshold values in response to a determined heart electrical activity signal variation of the patient. In one embodiment, the one or more heart cycle signal wavelets comprise Fourier components of the primary wave.

Processor 15 in step 623, stores in repository 17, predetermined mapping information associating predetermined thresholds and ranges of the amplitude representative values with corresponding medical conditions. The predetermined mapping information associates ranges of the amplitude representative values with particular patient demographic characteristics and with corresponding medical conditions and the system uses patient demographic data including at least one of, age weight, gender and height in comparing the ratio with the ranges and generating an alert message indicating a potential medical condition.

Comparator 20 in step 626, determines a comparison indicator indicating at least one of the amplitude representative values lies in a predetermined value range and compares the amplitude representative values with the ranges and corresponding multiple predetermined threshold values, to identify a medical condition. At least one of the predetermined threshold values is derived from recorded patient heart electrical activity signals for the patient. In another embodiment, at least one of the predetermined threshold values is derived from recorded patient heart electrical activity signals for a population of patients having similar demographic characteristics including at least two of, (a) age, (b) weight, (c) gender and (d) height, to those of the patient. In step 629, in response to the comparison with the ranges or a comparison indicating at least one of the amplitude representative values exceeds a respective predetermined threshold value, patient monitor 19 generates an alert message associated with the respective predetermined threshold or associated with a value range. The process of FIG. 6 terminates at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system performs multi-channel electrophysiological signal decomposition and wavelet pattern (vector) analysis and identifies the condition of individual anatomical sites in a 2D or 3D image representation of a heart. Further, the processes and applications may, in alternative embodiments, be located on one or more (e.g., distributed) processing devices on a network linking the units of FIG. 1. Any of the functions and steps provided in FIGS. 1-6 may be implemented in hardware, software or a combination of both.

What is claimed is:

1. A system for heart performance characterization and abnormality detection, comprising:
   an interface for receiving a signal representing electrical activity of a patient heart occurring during individual heart cycles of a plurality of sequential heart cycles;
   a signal processor for,
      decomposing the received signal into a plurality of signals comprising a heart cycle signal primary wave and one or more heart cycle signal wavelets occurring at corresponding successively higher frequencies and
      determining a plurality of amplitude representative values of said heart cycle signal primary wave and said one or more heart cycle signal wavelets;
   a comparator for comparing said plurality of amplitude representative values with a corresponding plurality of predetermined threshold values; and
   a patient monitor for in response to the comparison indicating at least one of said amplitude representative values exceeds a respective predetermined threshold value, generating an alert message associated with the respective predetermined threshold.

2. A system according to claim 1, wherein
said plurality of sequential heart cycles are successive heart cycles.

3. A system according to claim 1, wherein
said amplitude representative values of said heart cycle signal primary wave and said one or more heart cycle signal wavelets comprise at least one of (a) a peak amplitude, (b) a mean amplitude value, (c) a median amplitude value and (d) a root mean square amplitude value.

4. A system according to claim 1, wherein
said signal processor measures said plurality of amplitude representative values.

5. A system according to claim 1, wherein
said signal representing electrical activity of a patient heart comprises digitized sampled data values.

6. A system according to claim 1, wherein
said signal processor filters the received signal and segments the filtered received signal into heart cycle segments comprising an ST segment.

7. A system according to claim 1, wherein
said signal processor decomposes the received signal into a plurality of signals comprising a heart cycle signal primary wave and one or more heart cycle signal wavelets substantially occurring at harmonic frequencies of the primary wave.

8. A system according to claim 1, wherein
said one or more heart cycle signal wavelets comprise Fourier components of the primary wave.

9. A system according to claim 1, wherein
said successively higher frequencies comprise at least one of, (a) harmonics of the primary wave, (b) half-harmonics of the primary wave and (c) intermediate frequencies between harmonics of the primary wave.

10. A system according to claim 1, wherein
said comparator determines a comparison indicator indicating at least one of said amplitude representative values lies in a predetermined value range and
said patient monitor, in response to said comparison indicator indicating at least one of said amplitude representative values lies in a predetermined value range, generates an alert message associated with the value range.

11. A system according to claim 1, wherein
at least one of said predetermined threshold values is derived from recorded patient heart electrical activity signals for said patient.

12. A system according to claim 1, wherein
at least one of said predetermined threshold values is derived from recorded patient heart electrical activity signals for a population of patients having similar demographic characteristics including at least two of (a) age, (b) weight, (c) gender and (d) height, to those of said patient.

13. A system according to claim 1, wherein
said signal processor dynamically adjusts at least one of said predetermined threshold values in response to a determined heart electrical activity signal variation of said patient.

14. A system according to claim 1, including
a repository of mapping information, associating ranges of said amplitude representative values with corresponding medical conditions and
said comparator compares said amplitude representative values with said ranges to provide a comparison indicator identifying a medical condition and
said patient monitor generates an alert message identifying said medical condition.

15. A system according to claim 14, wherein
said predetermined mapping information associates ranges of said amplitude representative values with particular patient demographic characteristics and with corresponding medical conditions and said system uses patient demographic data including at least one of, age weight, gender and height in comparing the ratio with said ranges and generating an alert message indicating a potential medical condition.

16. A method for heart performance characterization and abnormality detection, comprising the activities of:
receiving a signal representing electrical activity of a patient heart occurring during individual heart cycles of a plurality of sequential heart cycles;
decomposing the received signal into a plurality of signals comprising a heart cycle signal primary wave and one or more heart cycle signal wavelets occurring at corresponding successively higher frequencies;
determining a plurality of amplitude representative values of said heart cycle signal primary wave and said one or more heart cycle signal wavelets;
comparing said plurality of amplitude representative values with a corresponding plurality of predetermined threshold values; and
in response to the comparison indicating at least one of said amplitude representative values exceeds a respective predetermined threshold value, generating an alert message associated with the respective predetermined threshold.

17. A method according to claim 16, including
associating ranges of said amplitude representative values with corresponding medical conditions and
comparing said amplitude representative values with said ranges to identify a medical condition.

18. A system for heart performance characterization and abnormality detection, comprising:
an interface for receiving a signal representing electrical activity of a patient heart occurring during individual heart cycles of a plurality of sequential heart cycles;
a signal processor for,
decomposing the received signal into a plurality of signals comprising a heart cycle signal primary wave and one or more heart cycle signal wavelets occurring at corresponding successively higher frequencies and
determining a plurality of amplitude representative values of said heart cycle signal primary wave and said one or more heart cycle signal wavelets;
a repository of mapping information, associating predetermined thresholds of said amplitude representative values with corresponding medical conditions; and
a patient monitor for comparing said amplitude representative values with said predetermined thresholds to identify a medical condition.

19. A system according to claim 18, wherein
said signal processor decomposes the received signal into a plurality of signals comprising a heart cycle signal primary wave and one or more heart cycle signal wavelets substantially occurring at harmonic frequencies of the primary wave.

* * * * *